(12) United States Patent
Pluvinage

(10) Patent No.: US 10,139,279 B2
(45) Date of Patent: Nov. 27, 2018

(54) APPARATUSES AND METHODS FOR BIO-SENSING USING UNMANNED AERIAL VEHICLES

(71) Applicant: BioSensing Systems, LLC, Salinas, CA (US)

(72) Inventor: Vincent Pluvinage, Atherton, CA (US)

(73) Assignee: BioSensing Systems, LLC, Atherton, CA (US)

(*) Notice: Subject to any disclaimer, the term of this patent is extended or adjusted under 35 U.S.C. 154(b) by 0 days.

(21) Appl. No.: 15/001,112

(22) Filed: Jan. 19, 2016

(65) Prior Publication Data

US 2016/0334276 A1    Nov. 17, 2016

Related U.S. Application Data

(60) Provisional application No. 62/160,493, filed on May 12, 2015.

(51) Int. Cl.
| | | |
|---|---|---|
| *G01J 3/28* | (2006.01) | |
| *G01N 33/02* | (2006.01) | |
| *G01J 3/02* | (2006.01) | |
| *G05B 15/02* | (2006.01) | |
| *B64C 39/02* | (2006.01) | |

(52) U.S. Cl.
CPC .......... *G01J 3/2823* (2013.01); *B64C 39/024* (2013.01); *G01J 3/027* (2013.01); *G01J 3/0264* (2013.01); *G01J 3/0297* (2013.01); *G01J 3/28* (2013.01); *G01N 33/025* (2013.01); *G05B 15/02* (2013.01); *B64C 2201/123* (2013.01)

(58) Field of Classification Search
CPC .... G01J 3/2823; G01J 3/0297; G01N 33/025; G05B 15/02; B64C 39/024; B64C 2201/123; A01G 25/16
USPC ........................................................ 700/284
See application file for complete search history.

(56) References Cited

U.S. PATENT DOCUMENTS

| | | | | |
|---|---|---|---|---|
| 5,471,056 A | * | 11/1995 | Prelat ...................... | G01V 8/02 250/252.1 |
| 6,422,508 B1 | * | 7/2002 | Barnes ..................... | F41G 3/14 244/3.15 |
| 6,587,575 B1 | * | 7/2003 | Windham .............. | G01N 21/31 250/458.1 |
| 7,058,197 B1 | | 6/2006 | McGuire et al. | |

(Continued)

OTHER PUBLICATIONS

International Search Report and Written Opinion in International Application No. PCT/US2016/031453, dated Aug. 31, 2016.

(Continued)

*Primary Examiner* — Thomas C Lee
*Assistant Examiner* — Alan Chu
(74) *Attorney, Agent, or Firm* — Nixon Peabody LLP

(57) ABSTRACT

Described herein are methods, apparatuses, and systems that enable a light weight autonomous unmanned aerial vehicle (UAV) to process hyperspectral (HSI) data during its flight and send information to the ground computer via radio-link. This capability is not currently available owing to the severe combination of technical constraints: the typical processing power required to analyze HSI data in real time; the small space and power available for the payload in a light-weight UAV; and the limited bandwidth available on the wireless link.

18 Claims, 5 Drawing Sheets

(56) References Cited

U.S. PATENT DOCUMENTS

| | | | |
|---|---|---|---|
| 2003/0193695 A1* | 10/2003 | Shirakawa | H04N 1/6086 358/302 |
| 2005/0151965 A1* | 7/2005 | Bissett, III | G01J 3/28 356/328 |
| 2007/0285422 A1* | 12/2007 | Nayar | G06K 9/4661 345/426 |
| 2008/0065286 A1 | 3/2008 | Han et al. | |
| 2012/0162428 A1 | 6/2012 | Wee | |
| 2013/0172691 A1* | 7/2013 | Tran | A61B 8/488 600/301 |
| 2013/0298083 A1* | 11/2013 | Bertoldo | G06F 3/0482 715/835 |
| 2014/0035752 A1 | 2/2014 | Johnson | |
| 2014/0140575 A1* | 5/2014 | Wolf | G06K 9/3233 382/103 |
| 2014/0160235 A1* | 6/2014 | Norland | H04N 7/18 348/37 |
| 2015/0015697 A1* | 1/2015 | Redden | G01N 33/0098 348/89 |
| 2016/0050840 A1* | 2/2016 | Sauder | A01B 79/005 701/3 |
| 2016/0069743 A1* | 3/2016 | McQuilkin | G01J 3/2803 356/416 |
| 2016/0133039 A1* | 5/2016 | Ritter | G06T 7/0042 345/629 |
| 2016/0232650 A1* | 8/2016 | Christ | G06T 5/007 |

OTHER PUBLICATIONS

Villafranca, A.G. et al., "Limitations of Hyperspectral Earth Observation on Small Satellites", Journal of Small Satellites, JoSS, vol. 1, No. 1, pp. 19-29, 2012.

Bareth, G., et al., "Spectral Comparison of Low-Weight and UAV-Based Hyperspectral Frame Cameras With Portable Spectroradiometer Measurements", Proceedings of the Workshop on UAV-Based Remote Sensing Methods for Monitoring Vegetation, Cologne, Germany, Sep. 2013.

* cited by examiner

APPARATUSES AND METHODS FOR BIO-SENSING USING UNMANNED AERIAL VEHICLES

CROSS REFERENCE TO RELATED APPLICATIONS

This application claims priority to U.S. Provisional Application No. 62/160,493 filed May 12, 2015, titled APPARATUSES AND METHODS FOR BIO-SENSING the contents of which are incorporated herein by reference.

FIELD

The present inventions relate generally to systems and methods for improving the food supply chain, and in particular to information systems that support the decisions and the choices made by participants to the food supply chain.

BACKGROUND

The human eye detects visible light in mostly three broad spectral bands, (red, green, and blue). Hyper-spectral sensors can capture images of fresh food items and provide detailed spatial and spectral information from the light they reflect. For example, when sunlight is reflected by a tomato or by a lettuce, the image captured by a hyper-spectral sensor provides the distribution of light intensities at many wavelengths across a two dimensional array of pixels. This information can be used to detect the shape of tomato or the lettuce as well as biological indicators correlated with the absorption and reflection spectrum of certain biological molecules in the tomato or lettuce across many narrow spectral bands measured by a hyperspectral sensor.

Instead of providing only the pixels' intensity variation using the broad color filters red, blue and green from a normal digital camera sensor, a hyper-spectral sensor may provide pixels with intensity variation measured in as many as 128 narrow band spectral filters or more. The number of usable bands is increasing, and is expected to increase in the future. The more bands, the more information that may be extracted. This level of resolution can be used by processing software to detect many characteristics that are not visible with a naked eye or a normal camera, ranging from the water-stress level of the plant to the presence of certain nutrients, fertilizers, insecticides, fungus, and others.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. The drawings are illustrative only, and that what is depicted therein may be adapted based on the text of the specification or the common knowledge within this field.

DETAILED DESCRIPTION

Figure 1:
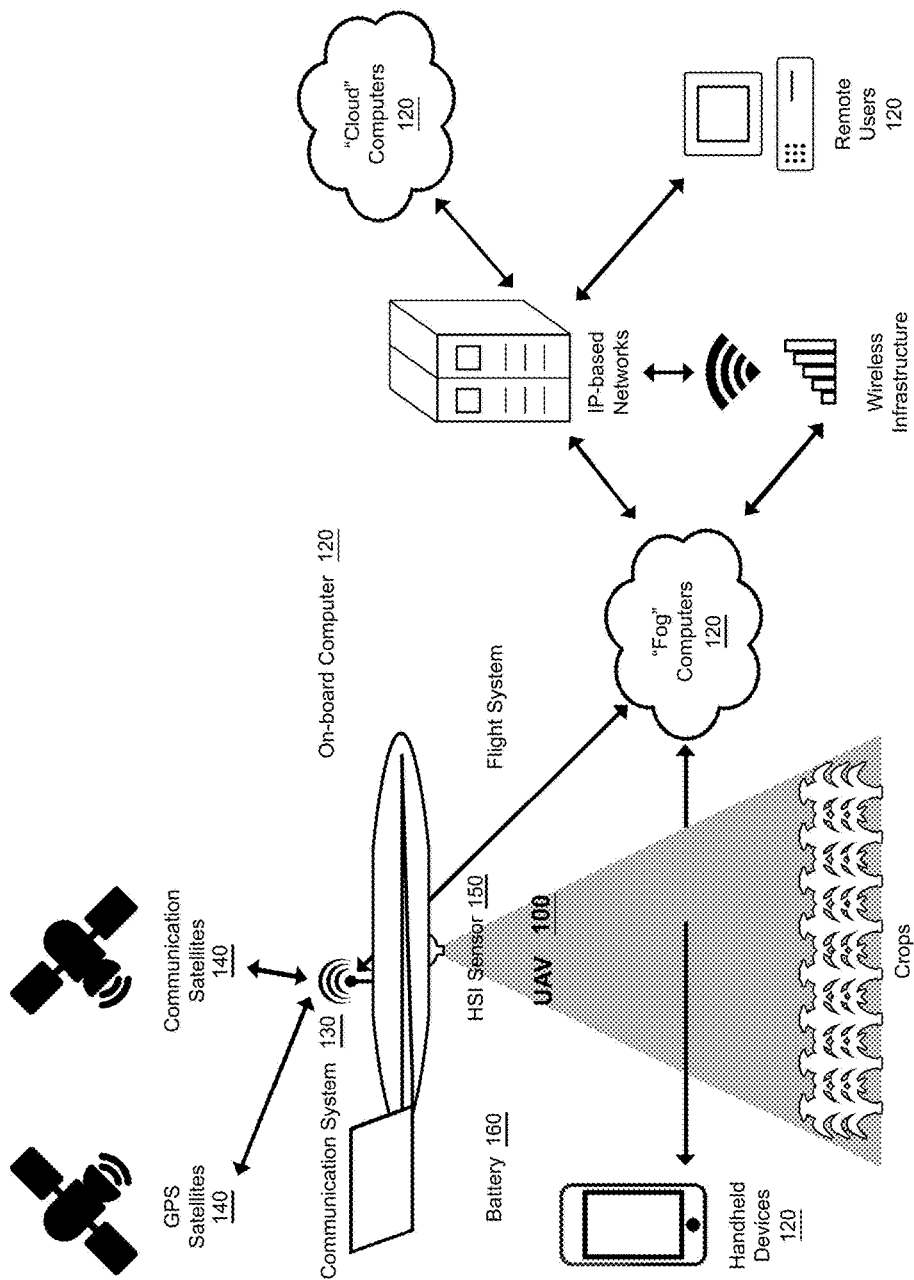
FIG. 1 depicts, in accordance with various embodiments of the present invention, a schematic diagram showing a system for using low cost hyperspectral imaging or "HSI" sensors on board aerial drones for surveying agricultural fields.

That the following detailed description is illustrative only and is not intended to be in anyway limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. In the development of any such actual implementation, numerous implementation-specific decisions must be made in order to achieve the developer's specific goals, such as compliance with application- and business-related constraints, and that these specific goals will vary from one implementation to another and from one developer to another. Moreover, such a development effort might be complex and time-consuming, but might nevertheless be a routine undertaking of engineering for those of ordinary skill in the art having the benefit of this disclosure.

While inventions described herein connect multiple types of sensors into a distributed information processing system, it is useful to first describe the inventions in the context of optical sensors capable of hyper-spectral imaging used in the production, processing, distribution, sale and consumption of fresh vegetables and fruits.

Hyper Spectral Sensors for Food

Hyper-spectral sensors can capture images of fresh food items and provide detailed spatial and spectral information from the light they reflect. For example, when sunlight is reflected by a tomato or by a lettuce, the image captured by a hyper-spectral sensor provides the distribution of light intensities at many wavelengths across a two dimensional array of pixels. This information can be used to detect the shape of tomato or the lettuce as well as biological indicators correlated with the absorption and reflection spectrum of certain biological molecules in the tomato or the lettuce.

Instead of providing only the pixels' intensity variation using the broad color filters red, blue and green from a normal digital camera sensor, a hyper-spectral sensor may provide pixels with intensity variation measured in as many as 128 narrow band spectral filters. The number of usable bands is increasing, and is expected to increase in the future. The more bands, the more information that may be extracted. This level of resolution can be used by processing software to detect many characteristics that are not visible with a naked eye or a normal camera, ranging from the water-stress level of the plant to the presence of certain nutrients, fertilizers, insecticides, fungus, and others.

While certain applications of hyper-spectral imaging have been used for decades in the food industry, recent developments have now made it possible to dramatically reduce the size, weight, power consumption and cost of hyper-spectral cameras, which allow the development of novel applications. For example, HSI sensors from IMEC (Belgium) commercially available can be less than a square inch and can be packaged in a fully functional camera module weighing less than 100 grams. The CMOS fabrication process leverages the wafer processing of standard semiconductor foundries, which can translate into very low cost (hundreds of dollars per sensor) at very high volume.

While many in the food industry can foresee, in general, the more widespread use of HSI sensors, there as yet have been no working solutions for practical application of the sensors on large scale projects. There remain significant barriers to the broad adoption of such new HSI sensors across the food supply chain. The very large scale of the food industry, combined with the very low margins experienced by many of its participants, represent an economic barrier that requires novel system designs beyond just the cost reduction of the HSI sensors.

The huge amount of data that each sensor can generate, combined with the large areas to be surveyed and the enormous number of food items processed each day, represent a technological barrier to data transmission and processing. The many participants in the food supply chain, combined with various regulatory and contractual obligations, represent a security challenge to the timely and secure access and sharing of information.

Shortfalls of Current HSI Systems

The use of HSI information to measure certain properties of fresh food items is well documented. However, systems and methods required to deploy such measurement systems in a scalable, cost effective, safe and secure way are needed. The use of hyperspectral imaging systems to measure characteristics of plants has been researched for decades, and numerous applications have been described in what has been recently known as the field of precision agriculture. HSI sensors and systems have been demonstrated in various configurations, ranging from automated machine sorting in processing plants to satellite or drone surveys of agricultural crops.

To date, however, the broad adoption of HSI technologies in the food supply chain have suffered from (a) the costs of the HSI sensors and systems; (b) the weight and power requirements of these sensors and systems; (c) the computational delays in providing ready-to-use information based on the processing of huge amount of raw data collected; (d) the lack of scalability across huge crop areas, huge processing plants, and complex logistics with many stakeholders.

Prior systems, such as Satellite-based HSI systems, can survey very large areas but with lower spatial resolution and significant processing delays, and cannot provide daily updates, with well documented limitations. See, e.g., *Villafranca, A*. et al. (2012): JoSS, Vol. 1, No. 1, pp. 19-29. Other systems, for example recent use of Octocopter-based HIS, do not have the range and the stability to fly autonomously and survey hundred acres an hour in windy conditions (for example 10 m/sec) often found in large crops. See Bareth, G., Bendig, J., Aasen, H., Gnyp, M. L., Bolten, A., Jung, A., Michels, R. 2013: "Introducing and Evaluating a Full Frame Imaging Spectrometer for Low-weight UAVs," Workshop on UAV-based Remote Sensing Methods for Monitoring Vegetation, Cologne, Germany 09/2013.

Yet other systems are equipped with multi-spectral cameras that do not have sufficient spectral resolution to properly detect and diagnose subtle changes in spectral signatures associated, for example, with rapidly spreading diseases like mildew. See Airinov MultiSpec 4C camera for SenseFly eBee. Simply put, the inventions disclosed herein solve a conundrum when compared with prior art: increasing the spectral, spatial and temporal resolution of the sensor imaging system, while enabling data processing to supply streams of actionable information at various speed designed to match the users' operational needs.

UAV Systems with HSI Sensors

Typically but not exclusively, crops are surveyed during the growth phase of the vegetables, up until the harvest time. The area to be harvested in a given week can exceed hundreds of acres, requiring the UAV to fly relatively quickly (10 meters per second or more) while the HSI sensors collects images of the plants with sufficient spatial and spectral accuracy to obtain the data required to make various decisions: irrigation, fertilization, detection of diseases, readiness to harvest, and the likes. A typical HSI sensor can generate a large amount of data per second, which can exceed the digital storage and computational power available on the UAV.

Transmitting wirelessly all of the HSI data while flying is in most cases not realistic, due to bandwidth limitation. Some of the information derived from the data collected by the HSI sensor may in one embodiment be transmitted while flying. For example, the data may be used to control certain actuators on the ground or to provide an opportunity for a human operator to make choices and alter the course of the UAV or the type of measurement requested.

Some of the information produced by the sensors may be compressed to fit within the on-board digital storage, while the rest may need to be discarded. The amount of computing power required to perform these tasks depends in part on the power efficiency of the on-board computer and the energy available from the battery, which must also support the navigation and communication systems as well as provide the energy for propulsion. Thus, it is apparent that the use of HSI sensors on agricultural UAVs to manage large planted crop areas require a careful balancing of many constrains: the hardware and software must be designed to optimized the local processing of the sensor's generated data flow, providing real time information about certain desirable field metrics and storing or discarding the rest based on the desired need for off-line analyses.

Processing In-Flight or Offloading to Ground Computer

In one example, hyperspectral sensors with sufficiently high spatial resolution (e.g., a four megapixel sensor, attached to a UAV flying at 10 m/sec, at an altitude of 60 meters above ground translates into a ground resolution of 2.5 cm) and with sufficient spectral resolution (e.g., 128 narrow bands of 4 nm from 600 nm thru 900 nm) have sufficiently fast frame rate (for example 100 frames per second) to provide overlap between frames. This translates into a very large amount of raw data: using the example just cited, more than 1 Terabytes of data is generated per hour. If this data is processed after landing in a batch mode, the results might be available only after many hours or days. Such a wait may be inadequate in meeting many of the requirements of a large-scale agricultural operation, where many decisions need to be made in less than an hour, and/or when plants harvested over hundreds of acres may be processed and send to the distribution channels within a short period of time, such as less than 24 hours.

In one embodiment, a software virtualization process may be used that enables the dynamic parsing of the tasks that are to be performed by the on-board computer and the tasks that can be off-loaded, either in real time or after landing, to a local computer nearby, which is denoted "fog computer". The word "fog" may be used to designate a local computer distinct from a server in a data center performing "cloud"

computing tasks. A fog computer may, in one example, be located on a truck near the fields being surveyed by the UAV.

Fog computers will likely be more powerful than the UAV on-board computer, and may include larger amount of storage and additional communication means. The fog computer may in one embodiment provide a wireless link to the mobile device (for example a tablet) held by a human operator in charge of the crops as well as connect with ground equipment and/or spraying drone(s). The fog computer may reside at the edge of a broader communication network, which may include cellular communication networks, packet switching networks, and/or satellite communication networks. Because the fog computer may be located closer to the UAV collecting HSI data, it can more easily send and receive data and commands with less latency and less powerful UAV transmission means. In addition, the fog computer may process information locally, which can reduce the data transmission rate and the latency required to communicate with cloud computers at the remote data centers. This is especially important in rural areas where high bandwidth wireless communications may be absent or too expensive.

For example, a GPS enabled "heat map" of selected variables may be output in order to be visualized on a tablet or other computer held by a field operator standing near the field surveyed, while the UAV is in still flying. This allows for re-routing of the UAV and changes in the surveyed characteristics based on the information just received, as well as changes to various operating decisions, ranging from sections to be irrigated, fertilized, harvested, etc.

HSI Hierarchical Data Processing for Field Operation Decision Support

In one embodiment, the data may be parsed and processed sequentially to produce near-real-time results (for example, during the flight); fast results (for example, less than about 30 or 60 minutes after landing); and slower results (over several hours, days, weeks, months and even years). Thus, the raw data may be managed to be processed in different ways at various locations, so that it can yield information used for a variety of purposes. For example, it may be used in the decision to immediately irrigate a section of the field or to avoid the harvesting of another contaminated section, to extracting medium term correlations between the plants grown in certain fields and their quality at the processing plant, or longer term correlations between weather and soil and the yield of certain seeds grown according to various protocols.

Field hyperspectral imaging may be systematically used to assess the multiple aspects of the crops during the growth phase up to the harvesting time, and to link the information collected to the hyperspectral imaging obtained at the processing plant where the harvested plants are cleaned, processed, packaged and shipped to various distribution channels. Typically, the food processor companies maintain traceability between the origin of the pallets collected in each of the fields and these pallets delivering the harvested plants at the conveyor belts loading these plants into each plant processing chain. The distance between the field and the processing plant, the timing and transportation conditions and other factors may affect the various characteristics of the harvested plants as they begin their journey through the food supply chain. A distributed data acquisition and processing process may therefore be created. This process may, for example, link hyperspectral data collected by cameras above the conveyor belts carrying plants in the processing plant with data collected from surveying the fields where these plants came from, during the growth and harvesting periods.

Hyperspectral Imaging Systems

Very recently, certain technology advances have enabled the commercial production of CMOS sensors that combine many attributes previously not available, such as: (a) multi-mega pixel special resolution; (b) large number of narrow spectral bands; (c) fast frame image capture; (d) low cost in high volume production.

For example, IMEC currently provides hyperspectral sensors with a spectral range from about 600 to 900 nm, a spectral resolution of less than 10 nm using approximately 100 to 128 narrow spectral bands, and 8×1024 pixels per spectral band. There are different types of hyperspectral sensors, including line-scan sensors and snapshot sensors.

Line-Scan Sensors

Line-scan sensors generally acquire more spectral information, as they use mechanism like diffraction gratings and mechanical parts to scan the full spectrum of each "line" of the image. Some line-scan sensors can scan 128 wavelengths, and therefore have high spectral resolution. However, because the image must be scanned, line scan sensors generally require sophisticated algorithms to combine multiple frames to reconstruct the spectral information of plants.

Snapshot Mosaic Sensors

Snapshot sensors generally acquire the entire image at once, with sensors that include multiple band pass filters arranged around the sensors. Mosaic hyperspectral sensors are advantageous because spectral and spatial information are collected at once in each frame, but at the expense of lower spatial and spectral resolution.

Sensor Incorporation

These new sensors may be incorporated in miniature cameras with standard mechanical lens mount (for example, "C-mount" to attach commercially available small lenses) and electrical interface (for example, USB 3.0 to feed the data to a processing computer) in a very small and light package. For example, a camera provided by XIMEA weight 27 grams, and its cubic shape is approximately 26 mm per side.

These new advances have opened up the possibility of new inventions, as discussed herein, using hyperspectral imaging techniques in a much more novel and ubiquitous ways to manage the quality, costs, and safety of food products. The technology itself, however, does not solve the major technical and business impediments to achieving these uses. One difficulty is often described as the "curse of dimensionality."

Consequently, the huge amount of data generated by the sensors leads to bottle necks in hyperspectral data processing, data transmission, and data utilization. Existing methods for reducing the dimensionality of raw hyperspectral data are not aimed at providing real time information using computing methods that meet the power and size limitations of lightweight UAVs.

Traditional approaches in hyperspectral remote sensing may rely on "unmixing" pixels based on supervised or unsupervised computation of "end-members" in the frames of the raw hypercube data sets. Some of the prior art describe various hardware acceleration based on FGPA, multi-core CPUs or GPUs. The unmixing is performed because the ground spatial resolution results in most pixels containing many "end-members" (for example, the pure spectral signature of a unique canopy sample).

Existing solutions that can be used on satellite or small aircraft are too bulky, power hungry and too slow to be used in the payload of a lightweight UAV to provide near real time information to a ground computer via a wireless link. As a result of these limitations, efforts to incorporate hyperspectral remote sensing in UAVs have taken the form of "batch mode" raw data processing: the hyperspectral camera collects the raw data and stores it immediately in local flash memory, such as SD-cards, which may be downloaded into a computer after the UAV has completed its mission and landed.

Furthermore, the computing power required to process the raw data with the solutions described in the prior art may typically be either too slow or too expensive in a field computer used in an industrial solution. As a result, these prior art solution may require the raw data to be transported or transmitted for processing at a central location and it is impractical to provide useful information extracted from the raw data immediately after the UAV has landed. Thus, the prior art does not provide the means to extract sufficient value either while the UAV is flying or immediately after landing to support the fast decisions that are typical of industrial operations harvesting many hundreds or even thousands of acres each week.

While there may be value in understanding long-term trends and correlations over days, weeks and months, there is even greater value in providing information that can be used just minutes or hours after collecting the raw data.

Classifiers

The invention described herein may utilize various machine learning algorithms or other classifiers to classify the data output from the hyperspectral sensor. For instance, various methods may first be utilized to reduce the dimensionality of the data, including principal component analysis (PCA).

In some embodiments, a quite simple classifier may be utilized to detected whether certain spectral bands cross certain thresholds after being identified as leaves, and/or direct reflect or indirect reflect leaves. In some embodiments, these could simply be whether a spectral band or a set of spectral bands crosses a threshold.

In other embodiments, various machine learning algorithms may be utilized to classify the data. For instance, various supervised learning models may be utilized that can be trained with data after an expert classifies the training data with known outcomes. For instance, Logistic Regression and Back Propagation Neural Networks may be utilized.

In other embodiments, linear regression modules may be utilized to classify image data in the spectral space. Accordingly, with such rich spectral information the models that may be utilized include a linear regression model. Other examples of regression include ordinary least squares regression, logistic regression, stepwise regression, multivariate adaptive regression splines (MARS), and locally estimated scatterplot smoothing.

Additionally, Bayesian Algorithms, Clustering algorithms, decision tree algorithms, association rule learning algorithms, and artificial neural networks. In some embodiments, the systems and methods disclosed herein will utilize the simplest algorithms possible for on-board calculations to save time and computing power, so that initial information and decisions can be made on-board. Then, after the UAV lands, more complex models could be run on the data to derive further information.

Unmanned Aerial Vehicles (UAVs)

Benefits of these inventions may be obtained by using autonomous drones or unmanned aerial vehicles (UAVs). These vehicles come in many shapes and sizes. The advantages and limitations of the UAVs are linked to a few key characteristics:

Span on a single flight. For a given amount of on board energy (for example, watt-hours of electrical energy stored in a battery), a fixed wind UAV may cover a much larger area in a single flight than a rotating wing UAV. The fixed wings UAVs may typically be able to fly in stronger winds, a significant consideration in open areas such as agricultural fields.

Altitude and resolution. The higher the flight, the greater the area "seen" at once by the on-board sensor, but the lower the ground spatial resolution (GSR) for a given lens optic. At lower altitude, a higher GSR can be attained, but faster frame rate is then required to achieve sufficient overlap between frames.

Regulatory considerations. Various countries have adopted or are in the process of adopting regulations as to the commercial operations of UAVs. In general, lighter UAVs flying at below an altitude ceiling with proper auto-pilot and ground controls have a greater chance of meeting the regulations or getting the case-by-case approvals required.

In one illustrative embodiment, one may use an eBee fixed wind autonomous UAV from Sensefly (Switzerland). For example, this UAV can fly at an altitude of 60 to 80 meters and cover on a single battery charge an area of 40 to 60 acres in less than 45 minutes, even in wind conditions up to 10 meters per second. Other UAVs may be used equivalently.

While such a UAV as the eBee can carry several types of camera payloads, ranging from high resolution RGB camera to lower resolution multi-spectral camera (insert specs), it lacks a hyperspectral camera payload. A hyperspectral camera is useful, for example, in detect mildew in spinach at an early infection stage and other types of key indicators. The challenges associated with incorporating a hyperspectral camera with sufficient spatial, spectral and temporal resolution include the weight and size payload limits as well as the total energy required for the camera and the on-board frame processing. For example, a payload energy budget of maximum 5 W allows the eBee UAV to cover sufficient acreage at sufficient resolution in a single flight. Increases in payload energy consumption reduce the flight time and the area covered during a single flight. One can combine the use of multiple UAVs, with the information collected in one UAV flying for example 50 meter altitude and 10 m/sec, being use to direct a second UAV flying at a lower altitude and slower speed to survey with greater precision and sensitivity a specific area of interest in a large field.

In the above eBee UAV example, the payload may comprise a hyperspectral CMOS sensor, incorporated into a miniature camera, together with a data processing, storage and communication board. It is a challenge to include the ability to process in real time the raw data collected by such a camera, so that useful information can be transmitted by radio link to a ground computer while the raw data is simultaneously stored on a micro-SD card. An example of the novel approach to solve this type of challenge is described next.

EXAMPLES

The examples below illustrate in more detail some embodiments of the inventions; however, they are for illustration and are not limiting. First is described an example of a UAV based system for implementing the disclosed invention.

FIG. 1 illustrates a UAV 100 carrying at least one hyperspectral sensor 150 that is directed to detect radiation (e.g. sunlight) reflected from the ground. As the UAV 100 flies over the ground at different altitudes and speeds, the hyperspectral sensor 150 may detect sunlight reflected from the ground (e.g. soil, crops) and output hyperspectral image data to the on-board computer 120.

The spectrum properties detected by the hyperspectral sensor 150 determine the wavelengths of the light absorbed by the objects it touched before being reflected back up to the UAV 100. The hyperspectral sensor 150 detects and outputs the intensity of each wavelength it for each pixel. Accordingly, the output image includes the intensities of each wavelength for each pixel for the entire image space.

The onboard computer 120 can perform various, filtering, processing, pre-processing and other functions on the hyperspectral data once output from the sensor 150. Accordingly, as disclosed herein, the on-board computer 120 may make various threshold, light weight calculations and to provide real time information or actionable items to be transmitted.

Accordingly, the UAV 100 may include a communication system 130 that transmits data to and from GPS and communication satellites 140, to handheld devices 120, and/or to "fog" computers 120. Accordingly, with these different communication options, the UAV 100 has several bandwidth and energy constraints as options, including wider bandwidth to handheld devices 120 and fog computers 120, while having reduced bandwidth but perhaps more robust or versatile communication with satellites 140. Accordingly, once initial processing is done, or a threshold determination is made, the UAV 100 may send an alert, a GPS enable heat map, or other information immediately to take action on to networked devices.

For instance, if certain areas of the crop field are suspected of having mildew after threshold processing of the image data, a GPS enabled map may be output that indicates warning locations that could be send to the handheld computer 120 or other device of a professional or additional UAV 100. Accordingly, either that professional or the additional, hovering UAV 100 could investigate further. In some embodiments, the lightweight UAV 100 may hoover and take closer and more detailed images of troubled zones to further evaluate the spectral properties.

Additionally, the communication system 130 can send data and or analyzed data with different priority to different systems for further analysis. For instance, after real-time threshold determinations are made, remaining data that is not discarded could be sent to various computers 120 (e.g., hand held devices 120, fog computers 120, or over the satellites 140 to servers 120, etc.). This may include data that requires further processing or could not be processed by the UAV 100 due to time constraints.

In some embodiments, the UAV 100 on-board computer 120 may include substantial memory for saving data that can be sent real-time, that can be stored for later processing on-board, or could be stored for downloading manually once the UAV 100 has landed. In some embodiments, the UAV 100 may only contain a memory, and the information can be downloaded once landed, and processed in the hierarchical, parsing manner as disclosed herein. In this embodiment, the UAV 100 may be even lighter because it does not require as robust of communication equipment or processing power. Accordingly, these systems and processing methods may be applied to the examples described below and others.

Example 1

Mildew Detection

Mildew is a fungal disease that may infect spinach and other crops. At first, the disease is difficult to spot using visual inspection, normal cameras, or even multi-spectral cameras (such as the MultiSpec 4C camera provided by Airinov). For instance, mildew may grow on the underside of the leaves where it does not receive as much direct sun exposure. Within a few days, the severity of the disease generally increases and begins to be visible. However, by the time it is easy to spot the presence of mildew visually, it is often too late as the spores have propagated across the field, carried by the wind, and infected a much larger area or possibly the entire field and adjacent ones. If the disease is not detected and the field is harvested, the diseased plants may be brought to the processing plant to possibly contaminate other batches. If the disease is detected after spreading, the whole field may need to be abandoned and the crops destroyed, resulting in an economic loss. The inventions described herein enable methods of early detection of mildew, and can provide the information very quickly to those in charge of inspecting the quality of the fields or deciding when to harvest. Further applications of this concept are disclosed herein.

Example 2

Precision Irrigation and Application of Fertilizers and Pesticides

Usable information may be supplied either in real time or near real time, to enable more granular watering of the crops, as well as reducing the amount of fertilizers and pesticides used across a field. By providing a gradient map of various indicators on a frequent and fast basis, the information can be used to direct ground equipment, either automatically or under human supervision, and apply varying amount of these agricultural inputs to match the variation of multiple indicators, measured frequently and simultaneously across the entire fields. It is possible to addresses the limitations that have prevented the broad adoption of hyperspectral imaging to support precision agriculture at an industrial scale. Since environmental factors such as sunlight, cloud cover, air temperature and humidity, and wind often vary from one hour to the next, it is critical for the processing of hyperspectral raw data to be fast enough to enable the precision irrigation, fertilizer application and, if necessary, localized spraying of fungicides.

Example 3

Crop Rows

Instead of applying complex algorithms in the manner described in the prior art to reduce the raw data dimensionality for the above and other applications, multiple sources of spatial and spectral a priori information may be used to simplify the immediate tasks required to provide useful information as quickly as possible while respecting the combined power, size and cost constraints that prevent the use of prior solutions. Accordingly, the following provides examples of algorithms that may be utilized to parse the data into tranches as described herein.

Figure 2:
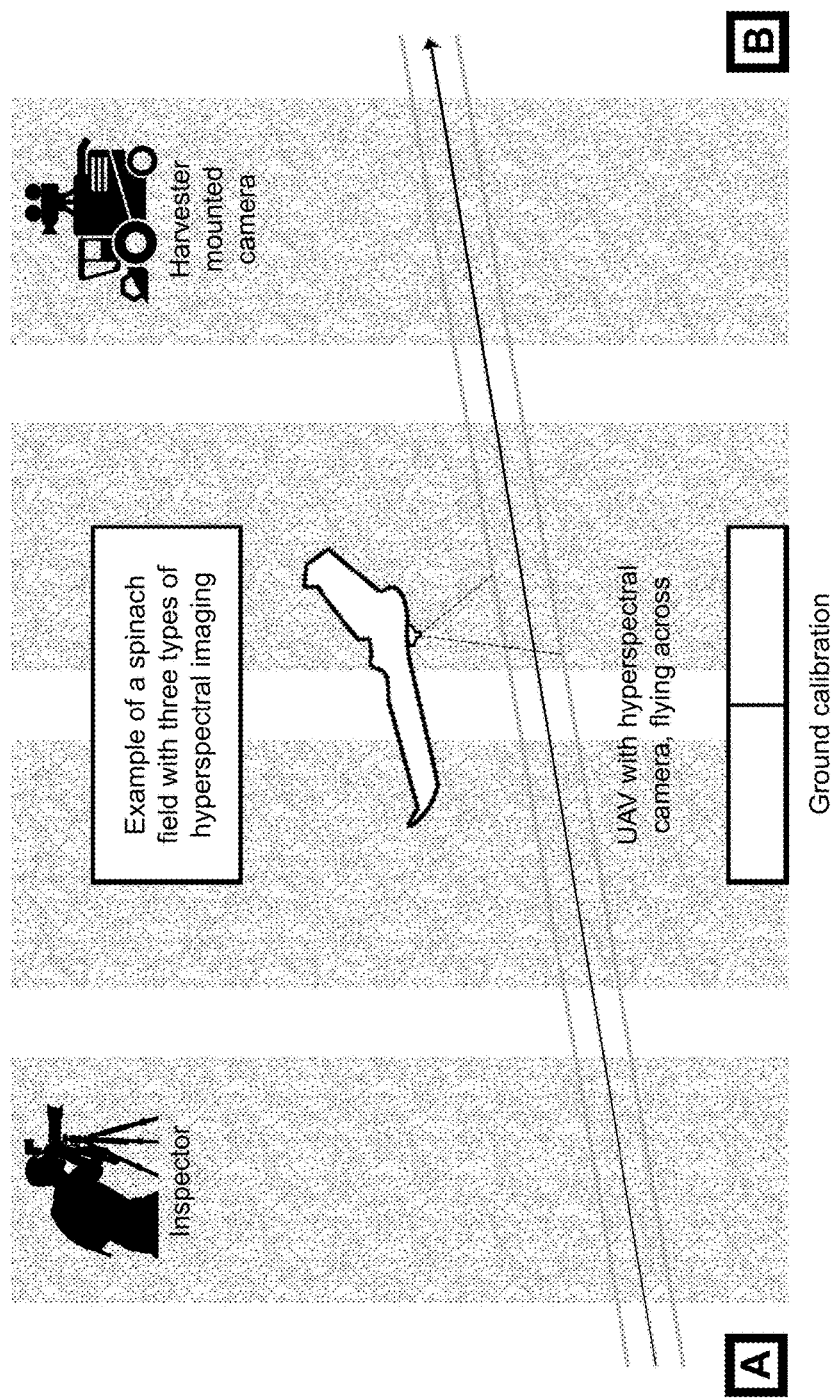
FIG. 2 depicts, in accordance with various embodiments of the present invention, an illustration of the measurement of aerial information in crop rows.

FIG. 2 illustrates an example of this approach. The figure includes "green bands" representing the rows of spinach plants, separated by "brown bands" representing the soil visible from the hyperspectral sensor 150 of the UAV 100, between the rows of spinach plants. FIG. 2 depicts a small section of a large field. In this example, the pitch distance between successive rows for spinach (i.e., the distance between the center of each furrow, is about 2 meters (about 80 inches), with the width of each furrow for the spinach canopy ranges between about 1.68-1.73 m (about 66 and 68 inches). Many agricultural fields, of various crops, have similar highly geometric and periodic patterns, due to the planting and harvesting equipment. Some fields have a two dimensional periodicity, for example in an orchard of almond trees, rather than the one-dimensional periodicity described in the spinach field example above. Some fields may need to be segmented into subsections, each exhibiting a regular geometrical pattern.

Of course, the GPS coordinates for entire field boundaries and the pitch of each crop may be known. For example, when a UAV 100 moves across the field at an altitude of 60 meters, a hyperspectral sensor 150 with two mega-pixels and an 18 mm focal lens may result in a GSR of 2.5 centimeters and a swath of 30 meters. Thus, the canopy image captured by the sensor may exhibit a very predictable pattern of alternating bands of "green pixels" and "brown pixels." Thus, the hyperspectral images output by the hyspectral sensor 150 (obtained, for example, as overlapping pictures with a snapshot sensor or video streams with a scanline sensor) may be vastly less complex than images from a satellite (where many pixels will be mixed because the GSR is much larger and many pixels will contain the reflectance from both soil and plants) or images from urban areas or natural landscapes (where the geometry may not be known and the number of end members may be much greater).

Accordingly, certain actionable information can be extracted from the raw data and significantly decrease the computational burden, by taking into accounts a priori information and leverage intrinsically sparse representations. For example, compressed sensing may be achieved by designing a special dictionary to described various segments of the images.

To illustrate this process, one may consider, as an example, the simplest image acquisition by a UAV 100 flying with a hyperspectral sensor 150 above a spinach field as described above. For simplicity, one can assume that the UAV 100 flies at a constant altitude and does not experience any roll, pitch or yaw: the sensor 150 is traveling parallel to the field. If the UAV 100 flies exactly perpendicular to the rows of spinach, each "green" pixel (i.e., pixels that are behind a Fabri-Perot cavity, in one embodiment, that permits a green portion of the visible spectrum pass through) on the sensor may fluctuate between "sensing" an image of the spinach leaves, projected by the lens, and "sensing" an image of the soil between the furrows.

Thus, the digital output of these "green" pixels, or pixels with a band-pass filter that passes wavelengths in the green spectrum, will oscillate between a higher number and a much lower number, based on the quantum efficiency of the CMOS sensor and the filtering in front of it. The periodicity of this "signal" may depend on (a) the speed of the UAV; (b) the pixel ground spatial resolution; and (c) the distance between furrows and their width. Similarly and simultaneously, the "brown" pixels of the sensor may produce a digital output that also "oscillates," producing a higher number when "sensing" the "soil" areas and a much lower number when "sensing" the spinach leaves. The output of the "brown" pixels would "oscillate" out of phase with the output of the "green" pixels, if one takes into account the very small delay between the position of the "green" pixels at one instant in time and the same position for the "brown" pixels at a slightly different time.

As used herein, the words "green" and "brown" are shorthand terms for spectra generally corresponding to crops and soil, respectively, and need not consist of any particular visible colors. Spinach leaves, for example, will have a certain spectral signature that is different from that of the soil between the furrows. In one embodiment, a support vector machine (SVM) may be used, based on some dictionary that projects the spectral signatures of the spinach and the furrows onto a smaller dimensional space. The spectral signatures contained in "a priori dictionary" can be specific to the phenotypes of specific plants. For example, a "green pixel" may be defined by spectral signatures that are different for a spinach plant from the spectral signature of lettuce plant. The spectral signatures stored in the "a priori dictionary" may even vary dependent on the type of spinach seeds used in a given field.

Classifying Pixels into Categories: (1) Green, (2) Brown, and (3) Mixed

For example, if one acquired, a priori, the average spectral signatures of the pixels exposed only to the image of the spinach leaves and of the pixels exposed only to the image of the soil, then a principal component analysis (or similar computation) could reduce the dimensionality of the spectral signatures from the relatively large number of bands on the sensor to just a few numbers sufficient to segment the images into sub-segment of pure: (1) spinach pixels and pure (2) soil pixels. The length of the vector representations of the two spectral signatures projected in that sub-space would then oscillate between high and low value. Of course, this approach assumes that there are many pure spinach pixels and pure soil pixels and very few mixed pixels. This is a direct consequence of a low flying UAV with a GSR much less than the width of the spinach furrow or the width of the soil between them.

Unlike satellite acquired images, where most of the pixels require unmixing to estimate the relative "abundance" of the pure spectra associated with elements of interest, one can construct a classifier that detects most of the: (1) pure spinach pixels and (2) pure soil pixels and ignores or separates into a distinct buckets pixels that are too far from these two end-members.

In a modified embodiment, we may now assume that the UAV 100 is flying exactly along the length of the spinach furrows. In this case, the "spinach vector" for the pixels sensing the spinach leaves will remain at a relatively high value during the time it takes the UAV 100 to fly from one end of the field to the other end, and the pixels that represent the soil between furrows will have a high value soil vector for about the same time.

The mathematics used to describe the above pixel output classifier can be generalized to take into account a UAV 100 flying at an angle greater than zero and less than 90 degrees with the direction of the furrows: the periodicity of the vector length oscillation may increase in a predictable way with the angle.

In practice, the UAV may experience some amount of roll, yaw and pitch, which may be detected and measured continuously by an auto-pilot and stored, along with the instantaneous GPS position and altitude, each time a picture is taken or a video frame is acquired. Thus, it may be a relatively simple matrix operation to project the acquired spectral vectors onto a manifold that preserves a priori geometrical information about the field and the flight. The a priori information, i.e., the known geometry of the field, may be used as a first approximation, and refined with relatively simple edge detection algorithms. The two signals oscillating out-of-phase as described above, can be used to compute the cross-over between the spectrally pure segment, as well as the approximate width of mixed pixels on each side the detected edge.

Instead of relying on matching features in overlapping images or frames to achieve a precise ortho-mosaic composite image, an on-board computer can assume that the edge between spinach furrow and soil is a straight line (at least over short to medium distances greater than the camera's swath at the prescribed altitude. Thus, the average spectral vectors for the soil and the spinach canopy can be easily computed from the segmented pixels, and the changes in these spectral vectors can be transmitted wirelessly with a great economy of computing power and bandwidth.

This allows for a tablet held by a ground operator to compute various indices linked to specific target information, such as the relative changes in water stress of the plants in the field, or the distinction between zones of healthy plants and zones of varying infection severity. Therefore, the information received from the UAV 100 can in one embodiment "paint" during the UAV 100 flight a GPS enabled "heat map" of these operational indices as color gradients superimposed on the map of the field. These "heat maps" can in one embodiment be further enhanced once the UAV 100 had landed and some of the raw data is used to augment the initial estimates.

In another example, a first level of segmentation of the spinach field may parse the pixels into "spinach canopy," "soil," "others," and "mixed" (pixels that are likely to be a combination of the prior three types). A second level of segmentation for the spinach canopy pixels may include "spinach leaves," "other plants," "fixtures," and "mixed." Thus, if the images captured by the UAV 100 include people working in the field and some equipment, the "dictionaries" may include signatures that are representative of each subcategory. These signatures may be based on prior spectral analyses (for example PCA of the spinach canopy); or based on the combination of spatial and spectral a priori information (for example the presence of metallic irrigation pipes in between each row of furrows); or based on information from other sources (for example the number of days since planting, combined with weather and irrigation information).

Example 4

Dividing Direct Light and Indirect Light Pixels Reflected from Crop Leaves

In another example, the pixel based spectral data output from the hyperspectral sensor 150 can be divided into pixels that are: (1) mixed, (2) soil, (3) direct sun leaves, and (4) shadowed leaves. The inventors have discovered that, analyzing the data reflected from crops, there are two distinct spectrums that result from light that is reflected from leaves. One of those spectrums appeared to be brighter than the other.

Figure 3:
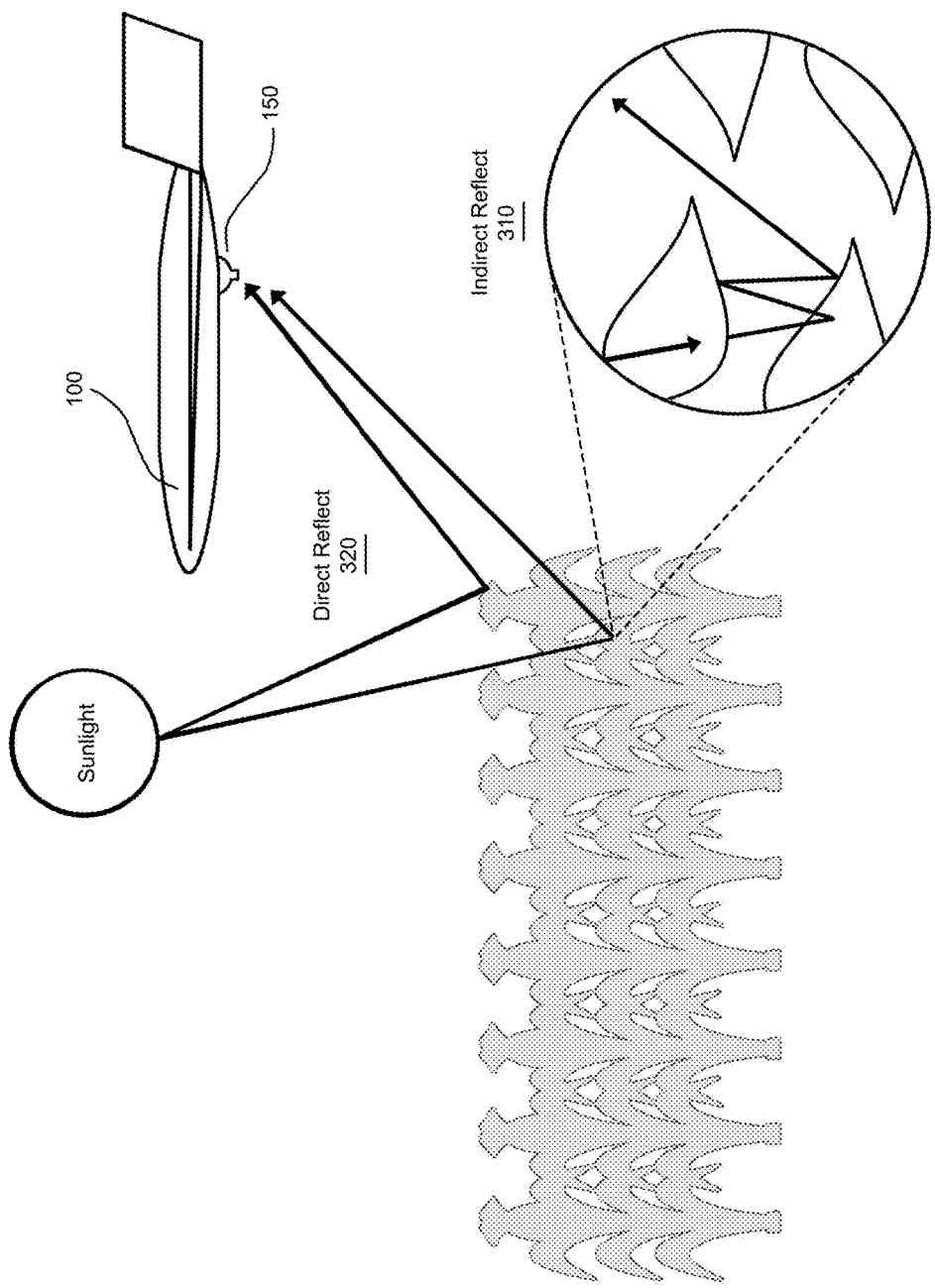
FIG. 3 depicts, in accordance with various embodiments of the present invention, a schematic view light rays from the sun directly reflecting to an HSI sensor on-board an UAV, and indirectly reflecting after bouncing off/passing through more than one leaf.

FIG. 3 illustrates an example of the light paths resulting in the two different spectrums. For instance, the sun may emit rays that are detected by the hyperspectral sensor 150 as direct reflect 310 light. Some of the other rays may pass through leaves and/or reflect on the underside of another leaf and then reflect back to the hyperspectral sensor 150 resulting in indirect reflect 320 light. Accordingly, it has been discovered that hypersectral sensors 150 were detecting light in each pixel from the sun that either:

A. Direct Reflect 310: reflected directly back from the leaves; or
B. Indirect Reflect 320: passed through leaves and reflected back on a second or third leaf (direct light pixels), or bounced off the underside of a leaf and then reflected back on a third or fourth leaf.

Thus, with this a-priori information, a principal component analysis or other dimensionality reducing formula can be applied to first separate the pixels into the appropriate buckets, by measuring, for example, the brightness of the green or other crop signifying spectral wavelengths or other spectral signals. For example, for pixels with very low crop vector brightness, they are likely soil or mixed and discarded. This could be a standard filter, a simple machine learning algorithm, or other computation. Then, or simultaneously, the crop pixels can be separated into (A) directly reflect and (B) indirectly reflect pixels for further analysis.

Next the data from direct and indirectly reflected crop pixels can be separately processed to make initial determination about, for example, (1) mildew contamination, (2) other disease problems, or (3) irrigation. Therefore, the number of pixels that will be analyzed in further detail (and in real-time for example) will be far less. Additionally, classifier algorithms applied to detect, for example, mildew on spinach could be much simpler when only classifying direct sunlight crop pixels or only classifying indirect sunlight crop pixels. This process is particularly useful for mildew, because mildew frequently begins growing on the underside of leaves. Accordingly, the indirect reflect 320 light detected by the hyperspectral sensor 150 may contain particularly valuable information.

Figure 4:
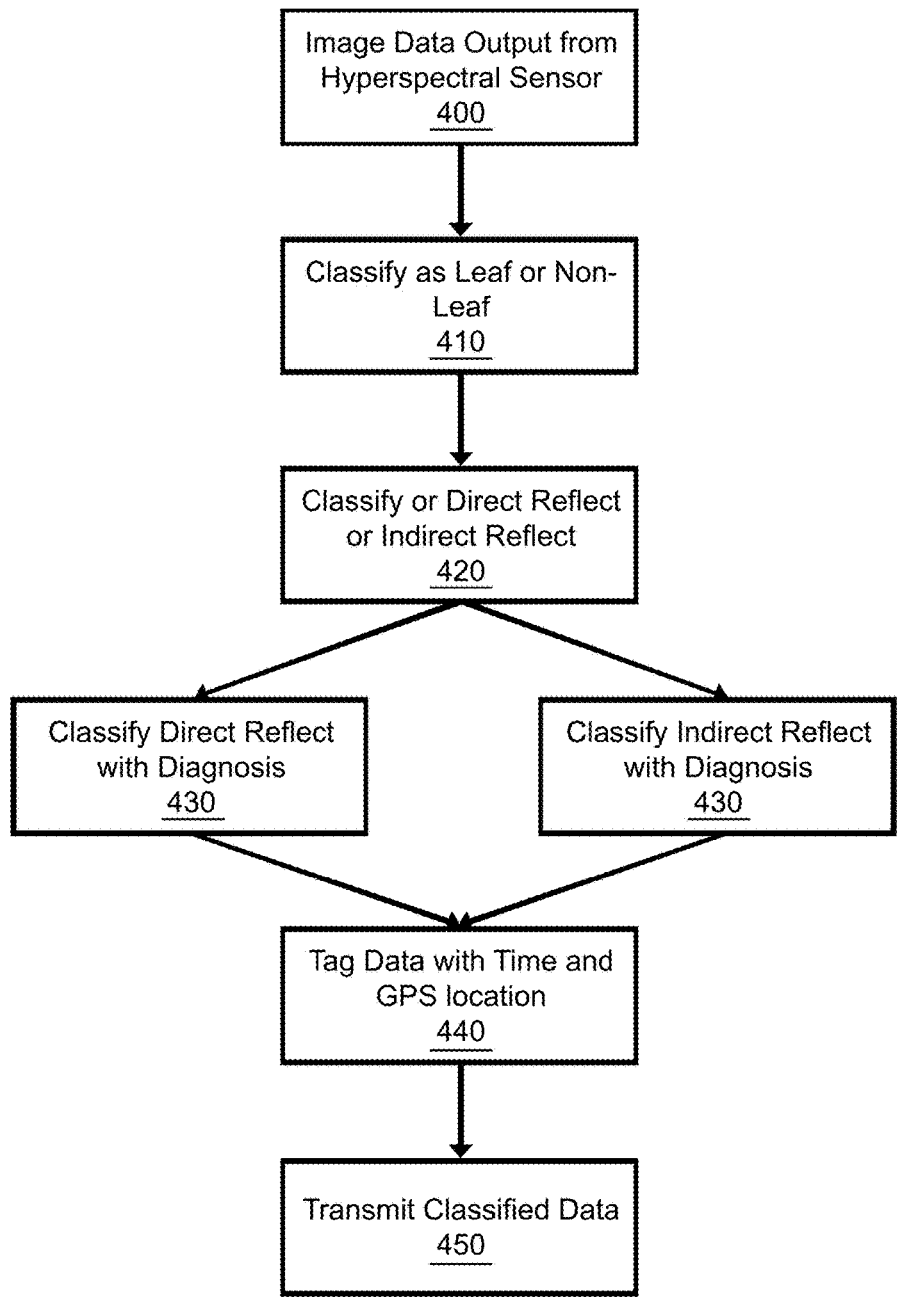
FIG. 4 depicts, in accordance with various embodiments of the present invention, a diagram showing a processing for classifying image data output from HSI sensors.

FIG. 4 illustrates an example of the process that could be used to make an initial classification of the pixels. For instance, image data output from the hyperspectral sensor 400 may be initially processed to classify pixels as leaves or non-leaves 410. Then, the pixels classified as leaves may be further classified as being direct reflect or indirect reflect pixels 420. Then, the direct reflect pixels and indirect reflect pixels may be separately classified to determine whether it is likely that plot has a disease 430. In some embodiments, this could be the detection of mildew 430.

In some embodiments, the classification step for determining whether the crops have a disease may be replaced with a step for determining the hydration levels of the crops 430. In other embodiments, the general health of the leaves may be classified, or ripeness of fruit (e.g. tomatoes).

After classifying the leaves (or fruit) with a diagnosis 430, the data may be tagged or otherwise associated with the time and GPS location 440. Then, the data may be transmitted 450 to a receiver on the ground or through a satellite connection remotely. In some embodiments, the system may only transmit data when the diagnosis step 430, determines that the crops have a disease (e.g. mildew), or that the hydration levels have crossed a threshold, so that action may be taken immediately, but the processing and transmitting can be preserved only for when necessary. In other embodiments, the system may continuously transmit the classification of the leaf pixels, regardless if the diagnosis 430 indicates action must be taken.

Example 5

Ground Calibration

In order to "acquire" the most relevant end-members prior to a flight, various techniques may be used. For example, the hyperspectral camera module that is to be used as payload on the UAV 100 may be used in a ground calibration procedure. The camera module may be attached to a linear scanning stage positioned at a fixed height (1 to 2 meters) above the spinach furrow, and moved horizontally perpendicular to it. Thus, a high-resolution image acquisition can then record at once the spatial and spectral information related to a specific field. In addition to recording images of the soil and spinach furrow from a short distance, one can in another embodiment, "scan" two "white target boards" (shown in the figure as "A" and "B" of FIG. 2) with known spectral reflectance. Since this data is acquired with the exact same camera module in the sunlight environment of the UAV flight, systematic equipment errors may be minimized.

Example 6

Air Calibration

In some embodiments, calibration may also take place with an additional camera mounted on the UAV 100 aimed towards the sky with a dome of known transmittance. Accordingly, this onboard calibration system will allow the UAV 100 to continuously recalibrate the system as the sun changes direction and intensity. Thus, the calibration camera may continuously take frames for calibration to recalibrate the system based on changing lighting conditions (e.g. sunlight changes, clouds, etc.). In some embodiments, the calibration camera may take 1 frame per second, 2 frames per second, 1 frame per minute, or other suitable amounts.

In some embodiments, a combination of ground and air calibration will be utilized, and an initial ground calibration will be used to calibrate the air calibration camera. Accordingly, this will allow the system to optimize the calibration of the on-board calibration system.

Figure 5:
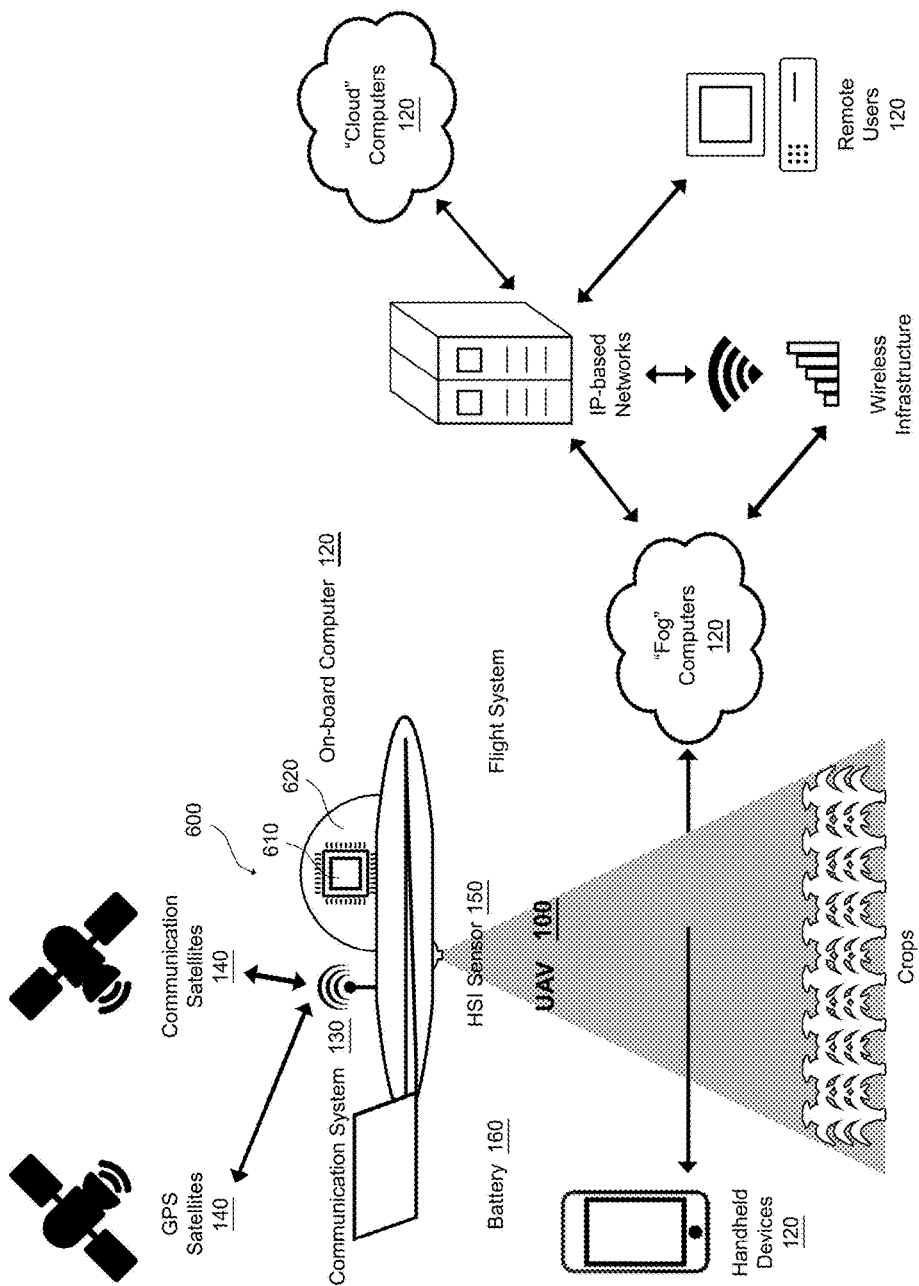
FIG. 5 depicts, in accordance with various embodiments of the present invention, a schematic diagram showing a system for using low cost HSI sensors on board aerial drones for surveying agricultural fields that includes an on-board calibration camera.

FIG. 5 illustrates an example of an on-board calibration system 600 that includes, for example a calibration camera 610 attached to the top portion of the UAV 100, and a calibration dome 620 that surrounds and covers the camera 610. The on-board calibration system 600 may include a dome 620 or other material of known transmittance that surrounds the camera 610 aimed at the sky or sunlight. Therefore, during operation of the UAV 100 the calibration camera can take images after light from the sun has passed through the calibration dome 620. Accordingly, the image data can be forwarded to the on-board computer and calibrated to the transmittance of the dome 620 utilized.

The calibration camera 610 may be a hyperspectral sensor 150 any may be the same hyperspectral sensor 150 as placed on the underside of the UAV 100. Therefore, there will be minimal differences between the calibration camera 610 and the hyperspectral sensor 150.

Therefore, regardless of changing conditions the hyperspectral sensor 150 will be recalibrated real time based on the calibration camera 610. In some embodiments, the calibration camera 610 may record time data that is time stamped and therefore the images can be recalibrated after the UAV 100 lands by calibrating the hyperspectral images 150.

Just after (in one embodiment) the short ground calibration procedure, which may for example take a short amount of time, such as 15 minutes or less, the field ground computer may process the data and compute the key a priori information required for the compressed sensing algorithm that will be processing the images during the flight. Thus, the higher processing power of the ground computer may simplify the task of the on-board processing electronics. This may enable a significantly lower processing power during the flight to produce very accurate real-time parsing and processing of useful information that can be sent on the UAV radio-link to the flight monitoring computer.

This procedure may not only enable a very small and light payload to process hyperspectral data while flying, but it also may greatly increase the accuracy of the information extracted. In addition to "segmenting" the pixels into "spinach furrow" and "soil," in-flight processing may also be used to further detect subtle changes between one area of the field and another.

Example 7

Training Classifiers

The ground calibration or training procedure described above may in one embodiment provide reference a priori information of the spectral signature of the specific spinach canopy grown in that specific field, and measure with the same sensor in the same sunlight on the same day. The field computer may thus process the spinach pixels from the ground calibration to extract a second set of end-members, distinguishing for example between the edges of the leaves and the center of each plant. In a tomato field, the planted segment of the calibration scan can in one embodiment be sub-segmented into "leaves" and "tomatoes". Note that this is a nested approach to image segmentation: first the pixels may be segmented into "soil" and "furrow," then next, the furrow pixels may be sub-segmented based on the spatial and spectral signatures of that portion of the images.

The GSR achieved during the ground calibration procedure may be much greater than the GSR achieved during the flight. However, the ground computer may know the height of the camera during the calibration procedure, and expected altitude during the flight. Thus, the "scaling effect" can be estimated prior to the flight, and used during the flight to classify pixels into segments and sub-segment, and estimate even small changes in spectral signatures.

The nested sequence of pixel segmentation based on a priori information, followed by the spectral vector signatures for each segment, can be repeated within each segment. For example, the furrow can be further segmented into sub-segment, each with its own spectral signature, leveraging the high-resolution data collected from cameras close to the ground to complement that of the UAV data. Ground hyperspectral camera 150 may in one embodiment be mounted on agricultural equipment (harvester, irrigation beams, fertilizer or pesticide dispensing machines, etc.). Field inspectors may also use handheld units to add high accuracy samples as specific locations, or to double check zones that have been flagged by the UAV 100.

The novel approaches to mix a priori spatial and spectral information, with nested processing of the various images or frames segments and sub-segments, may greatly reduce the computational tasks and enable much faster delivery of operationally useful information. In addition, the nested combination of using both spatial and spectral a priori information to segment images or frames, and leveraging support vector machines to compute changes in specific indices, also increases the ability to focus on getting greater accuracy in relative changes in certain indices from one region of field to another, irrespective of the data contained in other segments or without the need to compute abundances in mixed pixels.

Unlike typical research projects, where data is acquired once or a few times, and analyzed in batch mode, inventions described herein provide scalable solutions to address a system where hyperspectral data is acquired frequently with multiple scale modalities and combined with other non-imaging data, to "track" longitudinal changes in space (across a field or a series of fields) and in time (over hours and weeks). At each sensing stage, raw data may for example be parsed and compressed using nested segmented "dictionaries" based on prior spatial and spectral information.

The structure of the above data analysis need not require a significant amount of advanced modeling efforts. In fact, various modeling steps may be limited to the most common and elementary components, and then a sufficient amount of data may be used to train a neural network in extracting information and constructing an evolving set of dictionaries. For example, a set of dictionaries may be set up and fine-tuned to track four common diseases, along with water and fertilizer uptake, for a series of crops grown in large scale fields.

Example 8

Acquisition of Training Data for Classifiers

In some embodiments, to acquire classification training data for the classifiers, one may set up multiple plots of crops, some that are healthy and some at various time stages of a contaminate or disease. For instance, they could set up the following plots planting spinach:
(1) Healthy plot,
(2) Seeded one with mildew at week one;
(3) Seed one with mildew at week two;
(4) Seed one with mildew at week three Then, one could take three scans a day of each of the plots and use them as training data for the classifier. That way, the classifier could distinguish spinach pixels, or direct or indirectly light spinach pixels into various stages of mildew: (1) healthy, (2) week one mildew, (3) week two mildew, and (4) week three mildew, for example. Therefore, the classifier could not only detect mildew on crops in the beginning stages but also detect how far the disease has progressed, so a GPS enabled heat map can be output. For the mildew detected at a later stage of development, a higher priority indication to investigate those plots could be provided on a heat map. Therefore, agricultural professionals can investigate these higher priority areas first, as the mildew stage may be more advanced.

Classifiers (e.g., machine learning algorithms) may be further trained by expert annotation of identified areas. For instance, after the classifier identifies problem areas on crop fields, or on training plots, an expert could review the classifications and provide feedback on whether identified areas are actually infected with mildew. Therefore, the classifiers can continually improve and refined with additional training data. Furthermore, once the entire system is employed in a particular field, the experts can reclassify areas identified by the heatmap, so the classifiers deployed locally can be optimized for the conditions of that particular field and strain of crops.

Example 9

Combination Snapshot and Line Scanning HSI on UAV

In some embodiments, the present invention that includes both a snapshot hyperspectral sensor 150 and a scanning hyperspectral sensor 150. Accordingly, with both hyperspectral sensors 150 aimed at the crop field, the data for each pixel recorded can be matched between both cameras and provide additional information about each pixel. For instance, the scanning hyperspectral sensor 150 can detect a higher spectral resolution 150. The snapshot hyperspectral sensor 150 can detect a higher spatial resolution but usually has a lower spectral resolution (e.g. 25 different bands).

For instance, classifiers can be trained separately with each of the different image data and then the results can be combined to output disease or no-disease. In other embodiments, both types of image data from both hyperspectral sensors 150 can be input into the classifier at the same time to diagnose the state of the crops. For instance, as described above, many of the classifiers may rely on spatial information, and information output by the snapshot sensor may be utilized for spatial classification. Likewise, many of the classifiers described above (e.g. direct reflect versus indirect reflect leaves) rely on spectral information, and may accordingly be classified using information output from the line-scan sensor.

Example 10

Application of Principles Outside of the Field

The above principles may be utilized for many possible applications enabled by the present inventions. In particular, one can use low cost HSI sensors throughout the food supply chains. For example, such sensors can be used in one or more of the activity silos depicted, or others not depicted, including:
  in a UAV surveying the crops where vegetables are grown and harvested;
  in a processing plant where the vegetables are washed and packaged;
  in a truck transporting and delivery the vegetables to the retailers;
  at a retail display where consumers select and buy the vegetables; or
  at home where the vegetables are prepared and consumed.

Data, in raw and/or analyzed form, may flow back and forth between each activity silo. For example, information from the HSI chip 150 of a UAV 100 may be processed by a processing and communication module in a UAV 150 or nearby "fog" computing system 120 as described herein.

This processing may include machine learning algorithms or artificial intelligence, for example, or computer-assisted human decision making. The processing may be immediate or delayed, and may be proximate to the crop site, or on a remote server. The analytical data may be used to make decisions relevant to the grower or harvester, such as regarding irrigation, fertilization, or contamination. This analytical information may, for example, then be sent to a food processing plant, which may also use hyper-spectral imaging, processing, and decision-making in relation to issues such as washing, grading, and sorting. At each other activity silo, similar sensing, processing, and/or decision-making may be made, using that activity silo's own imaging and/or analytical data from other activity silos. Information may be passed either as feed-forward information, or as feedback. At each level, information may pass from sensors to processors, and then after analysis, from processors to actuators such as conveyor belts or irrigation systems.

Techniques described above for collecting hyperspectral data in the fields and parsing the raw data to provide real time (within seconds or minutes), immediate (within minutes or hours) and longer-term operational information, may also be applied at other steps in the food supply chain.

For example, after each field is harvested and the pallets are driven to the processing plant, the spinach plants may be unloaded into conveyor belts to be cleaned, cut and packaged. A hyperspectral camera 150 above each conveyor belt may "sense" the images at high speed and the subsequent data processing may apply similar techniques to enable immediate information to detect safety issues (for example the presence of fecal contamination) or quality metrics (for example the ripeness of tomatoes), while time stamping the data to allow for subsequent analysis of correlations between the field and the plant information. The nested data processing may match the needs of an industrial scale operation: some of the information, for example, can be used to reject certain batches or to bin certain plants according to quality, while other information can provide a feedback loop to modify the logistics between the scheduling of pre-harvesting harvesting.

When the power, volume, and weight constraints are the most drastic and demanding, the invention use specialized hardware that can use the proposed real time algorithms within the limited operating envelope required. For example, the eBee payload must be less than 30 mm×80 mm×100 mm, with a weight less than 150 grams and a power consumption less than a few watts (larger consumption comes at the expense of shorter flying time, hence smaller coverage area per flight).

The type of algorithm proposed above may, in one embodiment, be optimized with a special purpose image processor that combines a multiple parallel processing pipeline with one or two RISC cores. The various steps illustrated above (e.g., edge detection, image segmentation, support vector machines, etc., and equivalent methods) may in one embodiment be implemented by various vector operations working in parallel to mesh the sequence of pixel processing from across the sensor's spectral bands and spatial time sequence.

Based on experimentation and calculations, it is possible to calculate the required computing power of a particular system. For example, one may calculate the computing power required to process a 2 mega-pixel sensor, with 128 spectral bands (each 8 pixels by 1024 pixels) at a rate of 50 frames per seconds in a UAV flying at 10 m/s at an altitude of 60 meters with a 18 mm lens and a 30 mm GSR. The proposed algorithm may then be implemented with about 80 MFLOPs and less than 3 watts of total consumption, including the handshake with the autopilot (for GPS and other positioning data) and the coding for wireless transmission of compressed sensing indices using only 1 k bytes per second on the same radio link used for navigation control and reporting. Simultaneously with the real time processing, the raw frame data may in this embodiment be geo-tagged and stored on a 64 GB SD-Micro Flash memory for further processing after USB 3.0 transfer to the field computer post landing.

Similarly, such hyperspectral module can be used on the field equipment; above the processing plant conveyor belts; in distribution centers and even attached to tablets near the retail displays. The novel architecture may distribute the processing power to the edge of the overall system, such that real time information can be obtained using a priori information, and additional information can later be processed with more powerful computers located near the sensors or in data centers collecting information from the many data sources.

This novel hierarchy of hyperspectral processing, from real time low power processing at the sensing edges to fast medium power processing near the sensing edges to slower and higher power processing in data center, matches the needs of the food supply chain, increasing usability, scalability, and range of value creation, while reducing the traditional bottlenecks in computing power and data transmission.

One of the challenges of consolidating the data from in a very large number of sensors connected to distributed processing units is to maintain traceability of the data and the versions of software used between the sensors and the data centers. One example solution is to equip the field computers near the edges with an Iridium satellite link. Because this type of radio link is low bandwidth and expensive, it may be used to "upload" to the data centers the "data log stamp" (location, time, sensor type, processing type, etc.) as soon as collected. Thus, the central database can maintain the "status" of all data being collected, and the actual data may then be forwarded to the data centers at a slower pace.

For example, the field computer may be connected in the processing plant when the harvesting truck reaches it. The data may first be connected to the processing plant servers, and overnight uploaded to the centralized data centers. The Iridium link, which may work nearly everywhere on earth, can prepare the central databases and computers for the orderly data consolidation and batch processing. Some of the processing can proceed with partial data, and be enhanced later with additional data anticipated via the satellite data tag-forwarding channel.

The above systems anticipate that many stakeholders on the food supply chain would participate in the data collections, analysis and access to resulting layers of information. The systematic overview of data collected at the edges of the computing and communication networks, thanks to the universal tagging via satellite links, may provide the opportunity to "pre-sell" information before it is computed and even before the data is consolidated in the centralized data processing centers. Thus, while the "real time information" at the edge may have immediate operational value, the most expensive and extensive processing required to process in batch mode very large amount of data aggregated from many remote sources can be financed on an as-needed basis. A dashboard may be provided of the information available as soon as collected, but can move the data and process it later based on the willingness of various participants to pay for additional information. The costs of transmitting and processing vast amount of data may then be evaluated against the demand for the information that can be sold. One can imagine that certain participants may want to pay extra to be the first to obtain this information, and that it can be resold later at a lower price to others.

The invention creates a systematic way to collect, process, and forward data and information for different purposes: some of the purposes may be limited to precision agriculture; others may be used to optimize the supply chain and to provide retailers new ways to segment and differentiate products or consumers to optimize their taste or health habits; or even financial actors may want to pay for information to trade on trends or spot commodity markets.

The invention can first be deployed at the edges, where the value proposition is simple and immediate for those involved in agriculture. The real time information provided may have sufficient value to pay for the data collection system. Subsequent stages of deployment may then be staged based on providing additional value to stakeholders further down the food supply chain or even outside of it.

Thus, technical problems may be solved that have limited the board adoption of hyperspectral imaging. A technical framework is also provided that allows for profitably scaling up the entire system in staged, based on the information needs and willingness to pay of many participants.

Example 11

Feedback from Consumers and Distribution Channels

In the current food supply chain, there is limited information about food quality that is available to parties purchasing the end products, such as the retailers selling vegetables or consumers buying and consuming these vegetables. It may mostly consist of information contained in static labeling. Many food items have limited information provided on their packaging or in the display shelves, other than some product branding and regulatory compliant labeling. Described herein are apparatuses, systems, and methods to augment the information available to the recipients of the food supply chains, and to provide feedback loops to those producing and processing the food items.

In one embodiment, a small hyperspectral camera 150 may be attached to a tablet and positioned near the vegetable display in a supermarket. This camera can be used by consumers and retailer management to quickly "scan" fresh vegetables, much like one scans a bar code to obtain the latest pricing. The tablet may, for example, be linked to processing software and databases to offer an immediate display of nutritional information correlated with quality, freshness, safety, origin, and other useful characteristics. Depending on the needs and the interest of the person(s) using the hyperspectral imaging scanner, certain information may be more detailed and other may be omitted. This can be accomplished via a selection menu or even via wireless communication with an "app" on that person's smart phone. For example, certain consumers may be allergic to certain substances or have certain health care concerns or medical needs. Thus, the "hyperspectral scanner" not only can provide information that is specific to the exact food being scanned, but also can be personalized to the needs of the person using the scanner.

In one embodiment, an "opt-in" option may even enable the consumer to store the information about the food purchased, for example as part of a comprehensive diet management system. Such option may also enable the consumer to indicate at a later time other perceived characteristics, such as a grade for the taste of the food purchased, which could then be linked with the food scanned at the retailer's display and feed back to the processor's database, in an aggregate fashion with the feedback from other consumers. It is well known that taste varies amongst consumers, due to both genetic differences and variability in subjective preferences. There are multiple psychoacoustic techniques, such as multidimensional scaling, that can be used to group a subset of the population into preference clusters. Similarly, consumer with similar health needs, ranging from obesity to diabetes, and health restrictions, ranging from allergies to genetic enzyme deficiencies, may be "clustered." The suitability or subjective value of certain subset of the food items to each cluster may in one embodiment be mapped using information collected from the hyperspectral imaging along the food supply chains and the information provided, in an individual or in an aggregate manner, by the consumers. Ultimately, this type of information feedback loop may enable optimization of the practices of many of the food supply chain stakeholders and segmentation of the products to better market them to subsets of the consumers.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system for bio-sensing a predefined state of crops, the system comprising:
an unmanned aerial vehicle (UAV) equipped to collect hyperspectral images of a crop and at least one fog computer located near said crop,
said UAV and fog computer connected wirelessly to exchange and process crop-related data in real-time, said UAV comprising;
a hyperspectral sensor positioned on a bottom portion of the unmanned aerial vehicle and configured to collect and process image data of the ground during flight;
a control system connected to the hyperspectral sensor comprising one or more processors coupled to a memory, the control system configured to execute machine executable code during flight to cause the control system to:
receive the image data comprising a set of pixels from the hyperspectral sensor;
process the image data during flight to classify each pixel in the set of pixels as representing image data reflected from leaves and non-leaves to identify a subset of the set of pixels that represent leaves;
process the pixels classified as leaves during flight to further classify them as either direct reflect pixels or indirect reflect pixels;
parse additional processing tasks between the one or more processors onboard the UAV and one or more processors in the fog computer; and
said UAV and fog computer using software virtualization techniques to provide real time processing of the direct and indirect reflect pixels during flight to further classify them being in the predefined state by having a disease or not; and
said fog computer comprising a transmitter for transmitting hyperspectral data after a flight for further processing in remote cloud computers.

2. The system of claim 1, wherein the control system sends hyperspectral data representing the pixels classified as not being in the predefined state over the transmitter.

3. The system of claim 1, wherein the hyperspectral data representing the pixels classified as having a disease includes data representing the location.

4. The system of claim 1, wherein the hyperspectral data representing the pixels classified as having a disease includes a heat map.

5. The system of claim 1, wherein the control system sends the hyperspectral data only if pixels are classified as having a disease.

6. The system of claim 1, wherein the disease is mildew.

7. The system of claim 1, wherein the hyperspectral sensor comprises a scanning sensor.

8. The system of claim 1, wherein the hyperspectral sensor comprises a snapshot sensor.

9. The system of claim 1, wherein a linear regression algorithm is utilized to classify the image data as representing leaves having a disease or not.

10. The system of claim 1, further comprising:
a calibration hyperspectral sensor positioned on a top portion of the unmanned aerial vehicle; and
a calibration dome of known transmittance surrounding the calibration hyperspectral sensor.

11. The system of claim 10, further comprising: the control system configured to execute machine executable code during flight to cause the control system to:
cause the calibration hyperspectral sensor to capture calibration image data of sunlight passing through the calibration dome at regular intervals during flight; and
recalibrate the output of the hyperspectral sensor positioned on the bottom portion of the unmanned aerial vehicle after each interval based on the calibration image data.

12. The system of claim 11, wherein the regular intervals are one frame per second.

13. The system of claim 1, wherein the hyperspectral sensor comprises a scanning hyperspectral sensor and a snapshot hyperspectral sensor positioned on a bottom portion of the unmanned aerial vehicle and configured to collect image data of the ground during flight;

the control system connected to the scanning hyperspectral sensor and snapshot hyperspectral sensor comprising one or more processors coupled to a memory, the control system configured to execute machine executable code during flight to cause the control system to:

receive the image data comprising pairs of sets of images, each comprised of a set of pixels output from the scanning and snapshot hyperspectral sensors, each pair comprising one image detected by the scanning sensor and one detected by the snapshot sensor during overlapping time periods; and processing each pair of images during flight to map pixels from the image output by the scanning sensor to pixels from the image output by the scanning sensor, so that each pair of mapped pixels represents image data of approximately the same location on the ground.

14. The system of claim 13, wherein the control system is further configured to process each pair of mapped pixels to classify the mapped pairs as either representing image data reflected form leaves or image data reflected from non-leaves.

15. The system of claim 14, wherein the control system is further configured to process the pairs of mapped pixels classified as representing image data reflected from leaves as either direct reflect pixels or indirect reflect pixels.

16. The system of claim 15, wherein the control system is further configured to process the pairs of mapped pixels classified as representing image data reflected directly from leaves and separately process image data reflected indirectly from leaves to further classify the pixels as being in the predefined state by having a disease or not.

17. The system of claim 16, wherein the disease is mildew.

18. The system of claim 17, wherein the control system sends data representing the pairs of pixels classified as having a disease over the transmitter connected to the unmanned aerial vehicle.

* * * * *